United States Patent
Abels et al.

(10) Patent No.: US 7,094,052 B2
(45) Date of Patent: Aug. 22, 2006

(54) ORTHODONTIC BRACKETS WITH TEMPORARILY VISIBLE MARKING FEATURES

(76) Inventors: Norbert Abels, Alleestrasse 30a, 66424 Homburg (DE); Claus H. Backes, St. Wendeler Strasse 45, 66113 Saarbrücken (DE)

( * ) Notice: Subject to any disclaimer, the term of this patent is extended or adjusted under 35 U.S.C. 154(b) by 245 days.

(21) Appl. No.: 10/837,460

(22) Filed: Apr. 30, 2004

(65) Prior Publication Data
US 2005/0244776 A1    Nov. 3, 2005

(51) Int. Cl.
*A61C 3/00*      (2006.01)
(52) U.S. Cl. ............................. 433/8; 433/10; 433/11
(58) Field of Classification Search ............. 433/10
See application file for complete search history.

(56) References Cited

U.S. PATENT DOCUMENTS

| | | |
|---|---|---|
| 3,496,637 A | 2/1970 | Etengoff |
| 3,969,821 A | 7/1976 | Lee, Jr. et al. ............. 32/14 A |
| 4,050,156 A | 9/1977 | Chasanoff et al. |
| 4,120,090 A | 10/1978 | Kesling ..................... 32/14 A |
| 4,139,945 A | 2/1979 | DiGiulio .................... 32/14 A |
| 4,279,593 A | 7/1981 | Röhlcke ....................... 433/8 |
| 4,299,569 A | 11/1981 | Frantz |
| 4,415,330 A | 11/1983 | Daisley et al. |
| 4,551,096 A | 11/1985 | Dellinger |
| 4,626,208 A | 12/1986 | Hall ............................. 433/3 |
| 4,712,999 A | 12/1987 | Rosenberg ................... 433/8 |
| 4,867,679 A | 9/1989 | Rackley |
| 4,913,653 A | 4/1990 | Bolliger et al. ............... 433/3 |
| 4,952,141 A | 8/1990 | Wool |
| 5,074,783 A | 12/1991 | Reher |
| 5,238,402 A | 8/1993 | Röhlcke et al. ............. 433/2 |
| 5,322,436 A | 6/1994 | Horng et al. ............... 433/23 |
| 5,322,613 A | 6/1994 | Ohira ........................ 205/50 |
| 5,326,259 A | 7/1994 | Röhlcke et al. .............. 433/8 |
| 5,429,500 A | 7/1995 | Damon ....................... 433/10 |
| 5,439,378 A | 8/1995 | Damon ........................ 433/8 |
| 5,441,408 A | 8/1995 | Moschik ...................... 433/8 |
| 5,474,445 A * | 12/1995 | Voudouris .................. 433/10 |
| 5,542,844 A | 8/1996 | Perret, Jr. .................... 433/9 |

(Continued)

FOREIGN PATENT DOCUMENTS

DE        2903768        7/1980

(Continued)

OTHER PUBLICATIONS

Ormco Pulls It All Together, Ormco Corporation Brochure, 1990.

*Primary Examiner*—Ralph A. Lewis
*Assistant Examiner*—Casey Donahoe
(74) *Attorney, Agent, or Firm*—Workman Nydegger

(57) ABSTRACT

Self-ligating orthodontic brackets include a marking system for identifying which tooth or subset of teeth a specific bracket within a set of non-identical brackets pertains and/or for assisting in aligning a bracket on a tooth. The bracket includes a temporarily visible mark that is visible during placement of the bracket onto a tooth but which does not remain visible during long term use of the orthodontic bracket to straighten teeth. The marking may be removable or it may be hidden during use of the bracket to straighten teeth. The orthodontic brackets are advantageously included within a set or kit intended for placement onto the teeth of a patient. They advantageously include a ligation cover selectively movable between an open, non-ligating position relative to an arch wire slot in a bracket base and a closed, ligating position relative to the arch wire slot.

23 Claims, 7 Drawing Sheets

U.S. PATENT DOCUMENTS

| | | | |
|---|---|---|---|
| 5,551,319 A | 9/1996 | Spaulding et al. | 81/9.22 |
| 5,556,276 A | 9/1996 | Roman et al. | 433/8 |
| 5,595,484 A | 1/1997 | Orikasa et al. | |
| 5,692,896 A | 12/1997 | Pospisil et al. | 433/8 |
| 5,711,665 A | 1/1998 | Adam et al. | 433/9 |
| 5,716,208 A | 2/1998 | Forman | 433/8 |
| 5,803,728 A | 9/1998 | Orikasa et al. | 433/8 |
| 5,857,849 A * | 1/1999 | Kurz | 433/10 |
| 6,071,119 A | 6/2000 | Christoff et al. | 433/14 |
| 6,220,857 B1 | 4/2001 | Abels | 433/8 |
| 6,276,930 B1 * | 8/2001 | Pozzi | 433/9 |
| 6,347,939 B1 | 2/2002 | Abels | 433/10 |
| 6,394,798 B1 | 5/2002 | Huff et al. | 433/8 |
| 2002/0110774 A1 | 8/2002 | Abels et al. | 433/10 |
| 2002/0150857 A1 | 10/2002 | Orikasa et al. | 433/8 |
| 2002/0150858 A1 | 10/2002 | Jordan et al. | 433/9 |

FOREIGN PATENT DOCUMENTS

| | | |
|---|---|---|
| WO | WO03/061507 | 7/2003 |

* cited by examiner

ORTHODONTIC BRACKETS WITH TEMPORARILY VISIBLE MARKING FEATURES

BACKGROUND OF THE INVENTION

1. The Field of the Invention

The present invention relates to orthodontic brackets for use in orthodontic therapy. More particularly, the invention relates to orthodontic brackets that include one or more temporarily visible markings that facilitate placement of an orthodontic bracket on a tooth of a patient.

2. The Relevant Technology

Orthodontic brackets used for correcting dental malocclusions basically consist of a bracket base that includes one or more arch wire slots for holding one or more orthodontic arch wires therein. Customarily, an arch wire is held within the arch wire slot by ligatures. More recently, self-ligating brackets have been developed that eliminate ligatures. Self-ligating brackets may include a ligation cover associated with the bracket base that closes over and secures the arch wire within the arch wire slot.

In the practice of orthodontics, in order to maximize the effectiveness of treatment, individualized brackets are matched to each particular tooth, such that a bracket optimized for a particular tooth is generally different from a bracket optimized for another tooth. Because of the brackets' small size and similar appearance, confusion, frustration, and incorrect placement can result. Moreover, placement of the bracket in the correct orientation on the tooth can also be challenging.

What is needed in the art is an orthodontic bracket that includes temporarily visible features that permit an orthodontist or dental practitioner to match the bracket to a particular tooth or teeth of a patient to which it pertains and/or to properly align the bracket on a tooth.

BRIEF SUMMARY OF THE PREFFERED EMBODIMENTS

The present invention relates to orthodontic brackets that include a temporarily visible mark that is visible during initial placement of the bracket over a patient's teeth but which does not remain visible during long-term use of the bracket to straighten the patient's teeth. The temporarily visible mark may be removable or it may be located in such a way as to only be visible during initial placement of the bracket but so as to be hidden during long-term use.

According to one embodiment, the temporarily visible mark is a tooth-selection marking that allows an orthodontist or dental practitioner to match a particular bracket with the corresponding tooth, or subset of teeth, of a patient to which the bracket pertains. According to another embodiment, the temporarily visible mark is a bracket-alignment marking that helps an orthodontist or dental practitioner to properly position the bracket on a tooth. According to another embodiment, the temporarily visible mark may provide both functions of tooth selection and bracket alignment.

The inventive orthodontic brackets are generally included within a set or kit of orthodontic brackets that includes a plurality of differently sized and/or shaped brackets, each of which is suitable for placement on a particular tooth or a subset of teeth of the patient. In order to designate which bracket pertains to which of the person's teeth, the inventive brackets, according to one embodiment of the invention, may be equipped with one or more temporarily visible marks that indicate to a practitioner which tooth, or subset of teeth, the bracket pertains.

For example, one or more temporarily visible marks may be provided that indicate which quadrant of teeth (upper left, upper right, lower left, lower right) a bracket pertains. In one embodiment, a temporarily visible mark may designate or help define a grid divided into four quadrants representative of the four quadrants of a patient's teeth. A temporarily visible mark in a particular quadrant indicates which quadrant of teeth the bracket pertains.

In addition, the temporarily visible mark may also indicate which tooth within the designated quadrant the tooth pertains. For example, each quadrant in a mouth having a full complement of teeth will include up to seven teeth to which a bracket may be placed, including the incisors, canines, bicuspids, and molars position. A matching character (i.e., number or letter), design, other mark (e.g., dots), or combination thereof that can be used to match a particular tooth or subset of teeth within the quadrant onto which a particular bracket is designed to be attached during orthodontic treatment. By way of example, the number "3", or a group of three dots or other non-character marking, located in the upper right hand quadrant temporarily visible on the bracket, may be used to match the bracket with the canine (or cuspid) located in the upper right hand quadrant of the patient's teeth.

Once the orthodontist or dental practitioner has determined which tooth a particular bracket is to be placed, the bracket is then bonded to an appropriate surface of the tooth. In some cases, the bracket performs optimally when placed in a particular orientation on the tooth. According to one embodiment of the invention, the brackets may include one or more temporarily visible marks that help in properly aligning the bracket onto the tooth during bracket placement. According to one embodiment, the bracket-alignment marking includes a substantially vertical line that acts as an angulation axis while aligning the bracket on the tooth. According to another embodiment, the alignment mark includes a substantially embodiment, the alignment mark includes both substantially vertical and horizontal lines that help in aligning the bracket. Depending on their relative orientation, the substantially vertical and horizontal lines may define a grid having four quadrants, thereby also providing a tooth matching function, as discussed above (e.g., a tooth designation mark may be located in a quadrant defined by the horizontal and vertical alignment marks). In one embodiment, an arch wire slot may take the place of a horizontal line.

In addition to including one or more temporarily visible marks, brackets according to the invention preferably include a bracket base, an arch wire slot formed in the bracket base, and a ligation cover (i.e., the brackets are preferably self-ligating). The ligation cover can be selectively moved between an open, non-ligating position and a closed, ligating position relative to the arch wire slot. In a preferred embodiment, the ligation cover is attached to the bracket base by means of a hinge such that the ligation cover can be hingedly opened and closed relative to the bracket base as desired during placement and use. In the case where the bracket base and ligation cover are made from plastic, they can be molded as a single piece and connected together by one or more integral film hinges. In the case where the bracket base, ligation cover, or both are made from metal or dissimilar materials, the ligation cover may be attached to the bracket base by means of a mechanical hinge, such as a pivot pin or other hinge means known in the art. Of course it is certainly within the scope of the invention to provide any attachment means for temporarily or permanently attaching the ligation cover to the bracket base.

According to one embodiment, the temporarily visible mark comprises a removable marking on a labial surface of the ligation cover. The removable marking may be printed on the bracket cover with a water soluble ink that allows the marking to be removed once bracket placement is complete. After placement of the bracket, the water soluble ink may be rinsed away by the orthodontist or allowed to be washed away naturally when exposed to saliva in the patient's mouth. Alternatively, the removable marking may comprise temporary or permanent ink or printing applied to a removable decal that is temporarily attached to the labial surface of the ligation cover. After placement of the bracket, the removable decal is removed from the ligation cover and discarded.

According to another embodiment, the temporarily visible mark comprises a removable or permanent marking on a surface of the bracket base that is temporarily exposed when the ligation cover is in an open, non-ligating position. In the case where the marking is removable (e.g., comprises water-soluble ink or is printed on a removable decal), the temporarily visible mark on the bracket base can be removed as described above with respect to the removable marking on the labial surface of the ligation cover. Where the marking is permanent, the ligation cover is advantageously designed so as to cover the marking when moved to the closed, ligating position (e.g., the cover is large enough and sufficiently opaque to hide the marking behind the ligation cover during use while straightening teeth). Either way, the marking does not remain visible during use in straightening teeth.

According to yet another embodiment, the temporarily visible mark comprises a removable or permanent marking on the underside of the ligation cover. In the case where the marking is removable (e.g., comprises water-soluble ink or is printed on a removable decal), the temporarily visible mark can be removed as described above with respect to the removable marking on the labial surface of the ligation cover. Where the marking is permanent, the ligation cover is advantageously sufficiently opaque so as to hide the marking when the cover is moved to the closed, ligating position. In this way the marking is no longer visible because it is hidden under the ligation cover during use while straightening teeth.

According to another embodiment, the temporarily visible mark is placed onto, or forms part of, a removable auxiliary cover that fits over the bracket base when the ligation cover is in the open, non-ligating position. During bracket placement, the auxiliary cover provides the temporarily visible mark. After bracket placement, the auxiliary cover is removed from the bracket base and discarded.

Each of the foregoing ways of attaching or providing a temporarily visible mark comprises means for temporarily providing a mark on a bracket that is visible during placement of the bracket onto a tooth but which does not remain visible during use of the bracket to straighten teeth.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings, in which.

DETAILED DESCRIPTION OF THE PREFERRED EMBODIMENTS

Figure 1A:
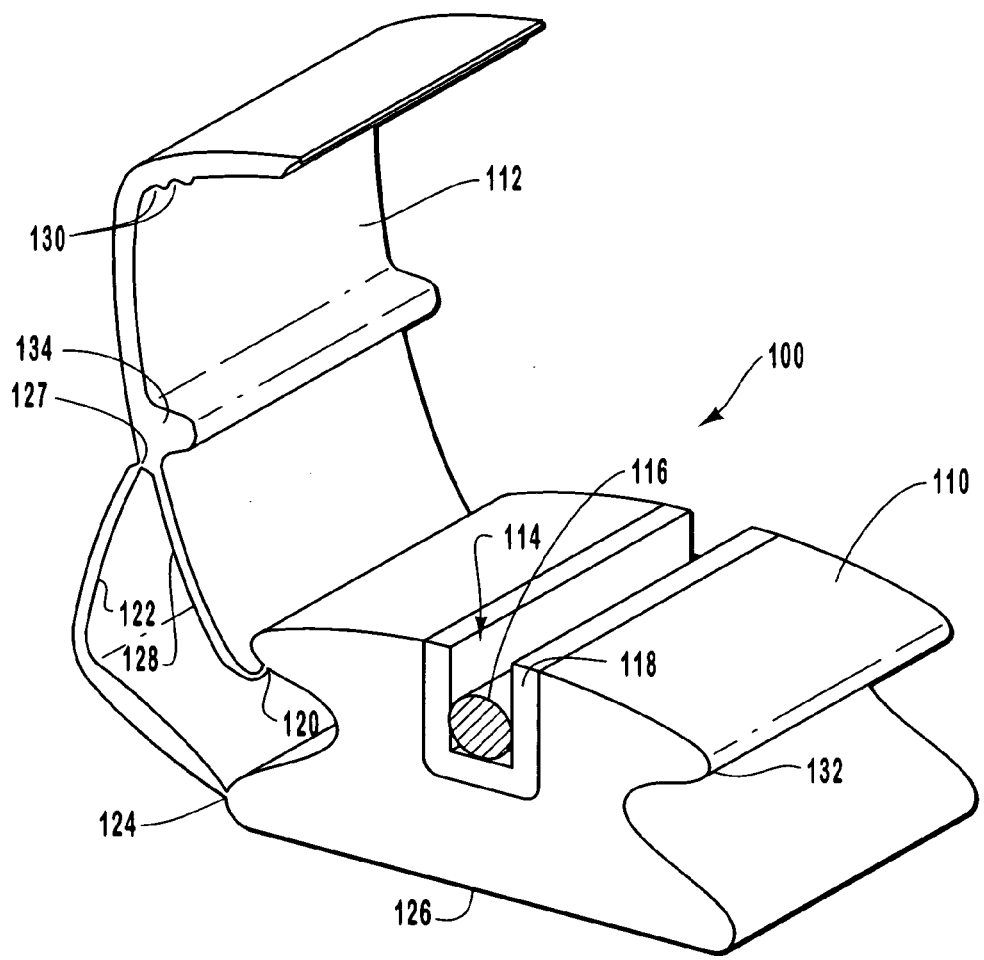
FIGS. 1A–1B are perspective views that illustrate an exemplary self-ligating orthodontic bracket comprising a bracket base, a ligation cover attached to the bracket base, and a temporarily visible mark on a labial surface of the ligation cover.

Brackets according to the invention include temporarily visible marks, which may include any suitable marking system that can be used for assigning a particular orthodontic bracket from within a set or kit of brackets to a specific tooth or subset of teeth and/or that can be used for aligning the bracket on a tooth. In one embodiment, the inventive brackets form part of a set or kit of brackets that includes one bracket for each tooth (28 brackets for the standard patient), although the kit can include any number of brackets, either smaller or greater than 28, as desired. In addition, the set or kit of brackets may consist of as many different types of brackets as there are teeth (e.g., 28 different types of brackets) or as few as 2 different types of brackets. In this way, the kit can provide a different type of bracket for each tooth, or it can use the same type of bracket for a subset of similar teeth. For example, it may be desirable to provide one type of bracket for molars, a second type for bicuspids, a third type for canines (or cuspids), and a fourth type for incisors.

The marking system may include graphics (e.g., an alignment grid), colors, characters (i.e., numbers or letters), non-character markings, (e.g., dots or hash marks), or a combination thereof. Examples include dots, hash marks, a letter (e.g., "i" for incisors, "c" for canines, "m" for molars, and "b" for bicuspids—other letters could be used depending on language or for any other purpose), a line, a number (e.g., 3 or a particular number of non-character markings for the number of the tooth from center), another marking, or any combination of the above. Of course, these examples are not exhaustive, and many other marking protocols are within the scope of the invention.

According to one identification convention, teeth are numbered in increasing numeric order starting with number 1 in the center of the upper or lower dental arch and increasing towards the molars. For an ordinary set of 28 teeth, each tooth receives a number between 1 and 7.

In one embodiment of the marking system, each of the upper and lower dental arches of the mouth is divided into two halves, thus forming a total of four quadrants for the whole set of teeth. The four quadrants are upper left, upper right, lower left, and lower right. Within each quadrant, the teeth are assigned characters (i.e., a number or letter) depending on their location relative to the center of the patient's mouth. Each tooth receives an identifying character (e.g., 1–7). The character is placed within a corresponding quadrant of an alignment grid. The alignment grid may comprise a substantially horizontal line, and a substantially vertical angulation axis or line that aid the practitioner in positioning the bracket correctly on a tooth. The lines may be offset relative to horizontal and vertical so as to correspond to the natural horizontal and vertical offset of a person's teeth (e.g., the horizontal and vertical lines may not be perpendicular to each other). The unique character and the positioning of the character within one of the quadrants of the alignment grid identify which tooth the bracket corresponds to. The substantially vertical line may include an arrow head pointing toward a particular location of the tooth (e.g, the incisal edge) to further assist in properly placing the bracket. To identify for which tooth a particular bracket is intended, the user first locates the alignment grid and determines whether the character lies within the upper left, upper right, lower left, or lower right quadrant. The user then determines which individual tooth or subset of teeth the bracket pertains to by identifying the unique character (e.g., 1–7).

In another embodiment of the marking system, each of the upper and lower dental arches of the mouth is divided into two halves, thus forming a total of four quadrants for the whole set of teeth. The four quadrants are upper left, upper right, lower left, and lower right. Within each quadrant, instead of assigning characters to each tooth, each tooth is assigned a number of dots or other non-character marks. The number of dots, or other non-character marks, corresponds to the tooth's location relative to the center of the patient's mouth. Each tooth receives an identifying mark comprising one or more dots or other non-character marks. The dots or other non-character marks are placed within a corresponding quadrant of an alignment grid. The dots and the positioning of the dots (or other non-character marks) within one of the quadrants of the alignment grid identify which tooth the bracket corresponds to. To identify for which tooth a particular bracket is intended, the user first locates the alignment grid and determines whether the dots or other non-character marks lie within the upper left, upper right, lower left, or lower right quadrant. The user then determines which individual tooth or subset of teeth the bracket pertains to. Examples of such alignment markings are included in FIGS. 6A–6D.

The present invention may be implemented in any desired self-ligating orthodontic bracket design. The bracket can be made of plastic, metal, ceramic, or other material or combination of materials. Generally an arch wire slot is disposed on or within the bracket base (commonly referred to simply as the "bracket" in the case of conventional brackets that do not include a ligation cover). A ligation cover is attached to the bracket (or bracket base) such that the cover is selectively movable between an open, non-ligating position and a closed, ligating position relative to the arch wire slot.

Each bracket includes one or more temporarily visible marks, which provide or comprise means for temporarily providing a mark on a bracket that is visible during placement of the bracket onto a tooth but which does not remain visible during use of the bracket to straighten teeth (hereinafter "temporary marking means"). According to one embodiment, the temporary marking means comprises a removable marking on a labial surface of the ligation cover. According to another embodiment, the temporary marking means comprises a removable or permanent marking on a surface of the bracket base that is temporarily exposed when the ligation cover is in an open, non-ligating position. According to another embodiment, the temporary marking means comprises a removable or permanent marking on the underside of the ligation cover that is visible when the ligation cover is in an open, non-ligating position. According to another embodiment, the temporary marking means comprises or forms part of a removable auxiliary cover that is positioned over the bracket base during bracket placement and that is removed and discarded after placement. The following examples are to be considered in all respects only as illustrative and not restrictive. They are intended to give a general understanding of some applications of the present invention.

Figure 1B:
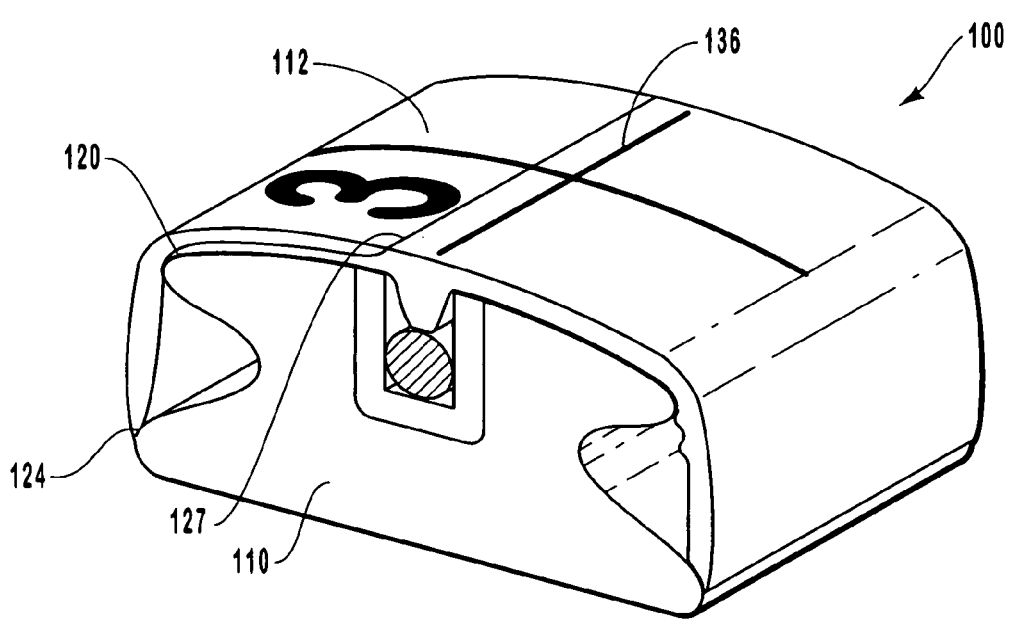

An exemplary orthodontic bracket as shown in FIGS. 1A–1B can be manufactured in a single integral piece as an injection molded plastic part. The orthodontic bracket 100 has a base 110 to which a cover 112 is hingedly connected. An arch wire slot 114 open to the upper side of the base 110 is provided near the center of said base 110 and serves for the insertion of an arch wire 116 therein. A reinforcement insert 118 may optionally be provided with the slot 114. The reinforcement insert 118 may be formed from a metal or more rigid plastic material and generally has a U-shape in cross-section. The basic material of the bracket can be molded around the optional reinforcement insert 118 in the manufacturing process. The arch wire 116 can have a cross-sectional area that is round, square, or any other suitable shape. In FIGS. 1A–1B it is illustrated with a round cross-section and is arranged inside the slot 114 and serves to correct the teeth in a known manner.

Although cover 112 is shown as being hingedly connected to the base 110, the cover could be attached by in any desired manner, by e.g., a pivot pin, a flexible latching cover without a hinge, by a chain or other tether, or any other attachment means known in the art. In the embodiment shown, the cover 112 is attached to the base 110 by a flexible film hinge of reduced materials cross section. The ligation cover 112 depicted in FIGS. 1A–1B forms a curved hood and is connected in one piece to the base 110 via an integral hinge 120. The hinge 120 in this embodiment is a localized area of reduced cross sectional thickness.

A spring element 122 with an approximately L-shaped cross-section is hingedly attached via a joint 124 in the region of the bottom 126 of the base 110. That is, the spring element 122 may be attached via an integral hinge that may be formed in the same way as the integral hinge 120, i.e., by a corresponding reduction in the material cross-section during injection molding. The spring element 122 may be further hinged to the outside of the cover 112 via a further integral hinge 127 of the same design.

One or more locking recesses 130 may be provided on the inside of the cover 112. The locking recesses 130 enable the cover 112 to be able to latch onto a closing nose 132 of the base 110. Furthermore, a bearing protrusion 134 may be provided on the inside and middle of the cover 112 in order to bear against the arch wire 116 within the slot 114 when the cover 112 is in a closed state.

On the labial surface of cover 112 is a removable marking 136 that, in this exemplary embodiment, designates or identifies the tooth to which the bracket pertains (e.g., the number "3" in the upper left hand quadrant of a grid indicates that the bracket pertains to the canine or cuspid in the upper left hand quadrant of the patient's teeth). Thus, the marking 136 communicates to an orthodontist or dental practitioner to which tooth the bracket is to be affixed. The removable marking 136 in this exemplary embodiment also includes an alignment grid that can be used in properly orienting the bracket 100 onto a tooth.

The removable marking 136 may be printed on the labial surface of the ligation cover 112, such as with a water soluble ink that allows the marking to be removed once bracket placement is complete. After placement of the bracket onto a patient's teeth, the water soluble ink may be rinsed away by the orthodontist or allowed to be washed away naturally when exposed to saliva in the patient's mouth. Alternatively, a removable decal bearing the marking 36 can be placed on the surface of the ligation cover to aid in bracket placement and then removed and discarded after placement.

Figure 2A:
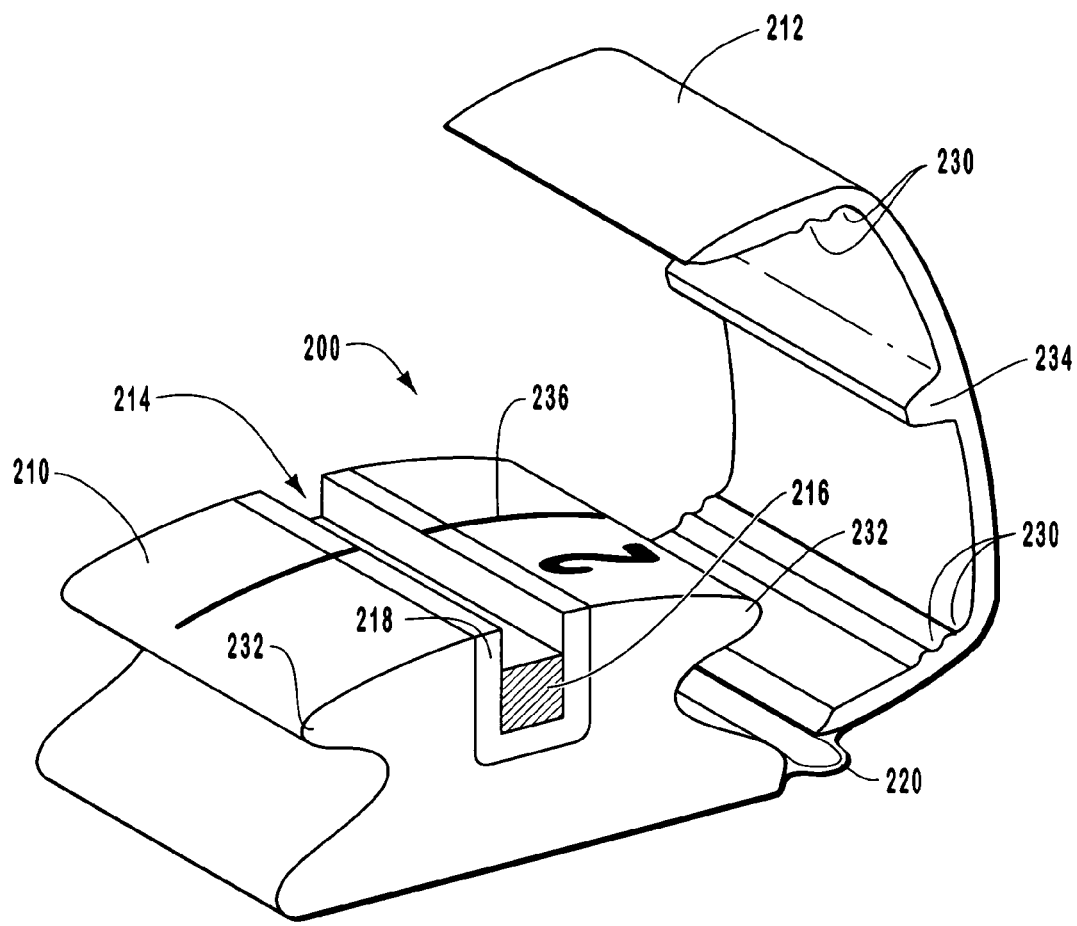
FIGS. 2A–2B are perspective views that illustrate an exemplary self-ligating orthodontic bracket having a temporarily visible mark on a surface of the bracket base that is exposed while the ligation cover is in an open, non-ligating position.
Figure 2B:
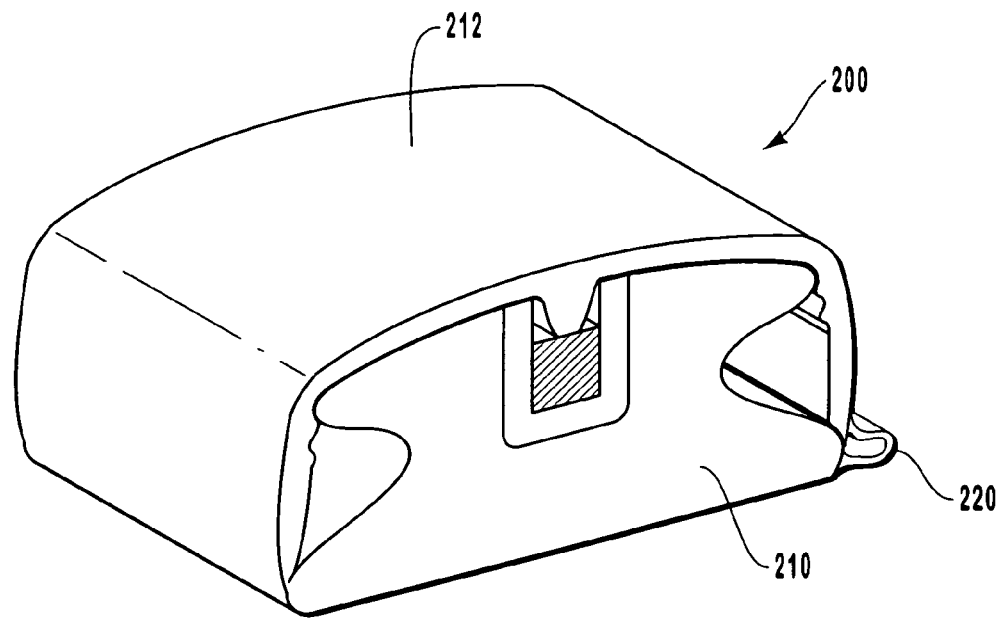

An alternative example of a bracket 200 implementing the invention is shown in FIGS. 2A–2B. Bracket 200 is similar to that illustrated in FIGS. 1A–1B in that it includes a bracket base 210, a ligation cover 212, a slot 214, an arch wire 216, a reinforcing insert 218, one or more locking recesses 230, a closing nose 232, a bearing protrusion 234, and an alignment marking 236. This example differs from that illustrated in FIGS. 1A–1B in that it uses a strap hinge 220, which is a film hinge of elongated reduced cross section.

In addition, this example also differs from that illustrated in FIGS. 1A–1B in that it includes a temporarily visible mark 236 (which may be either formed with removable or indelible ink) on a surface of the bracket base 210 that is temporarily exposed when the ligation cover 212 is in an open, non-ligating position. The temporarily visible mark 236 is either removable or not visible during long term use of the bracket 200 to straighten teeth when hidden behind the ligation cover 212. The alignment grid of the temporarily visible mark 236 is formed by a substantially vertical line with the arch wire slot 214 forming the substantially horizontal line of the alignment grid. A printed horizontal line could alternatively be used.

The bracket illustrated in FIG. 2A is shown with a numeral "2" in the lower left quadrant of the alignment grid, indicating that this bracket is intended for use on a tooth of the lower left quadrant of the patient's teeth. The "2" indicates that the bracket is intended for a tooth corresponding to the number "2" (e.g., the second incisor in the lower left quadrant of the patient's teeth).

Figure 3A:
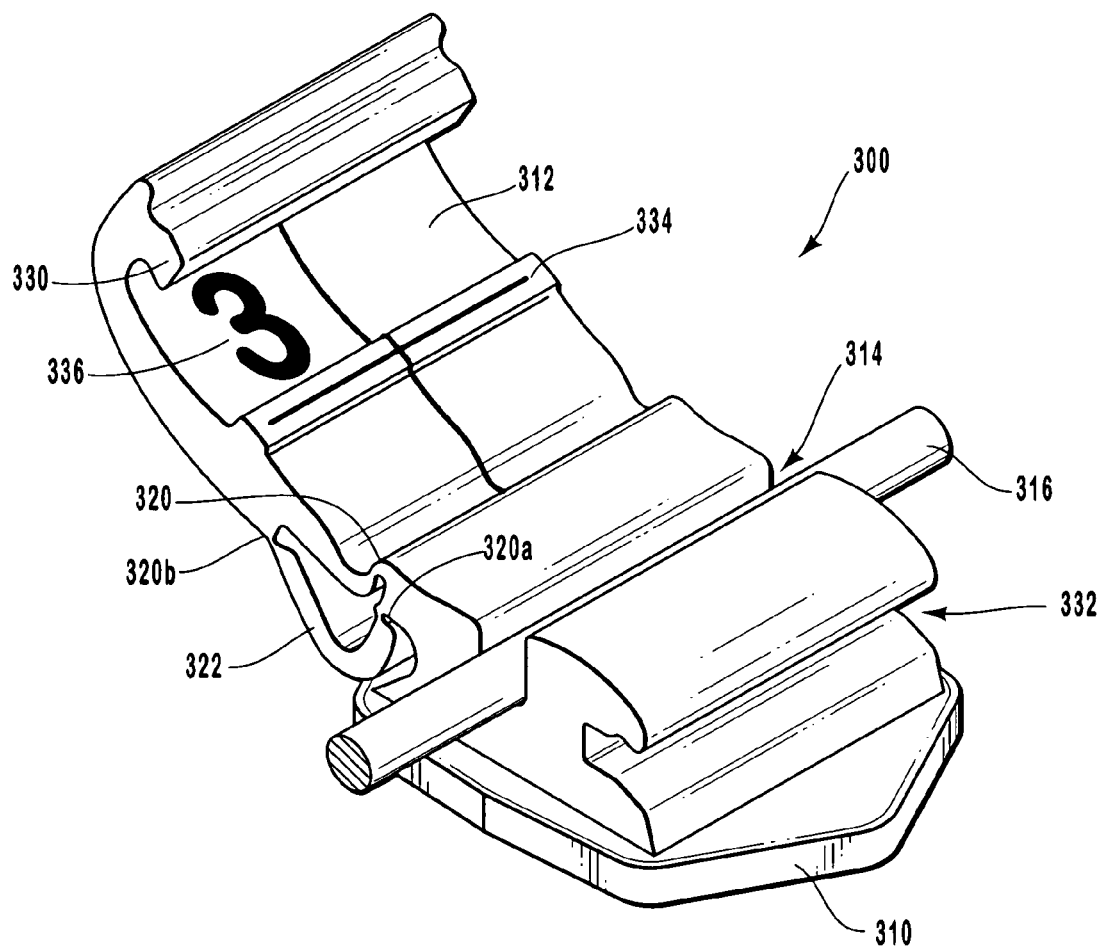
FIGS. 3A–3B are perspective views that illustrate an exemplary self-ligating orthodontic bracket having a temporarily visible mark on an underside of the ligation cover.
Figure 3B:
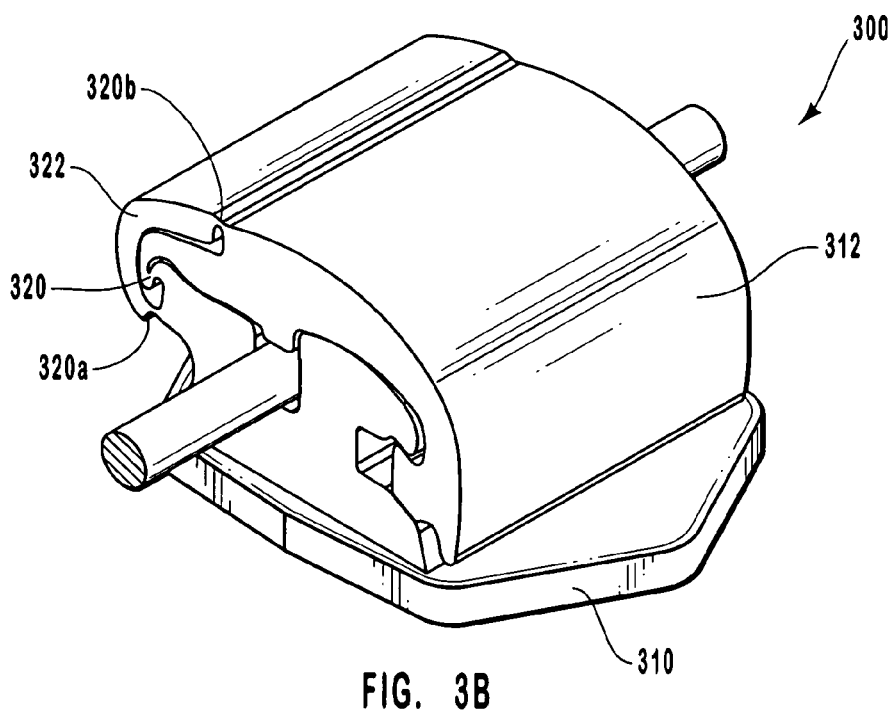

Another example of an alternative bracket 300 implementing the invention is shown in FIGS. 3A–3B. This bracket includes a base 310, a ligation cover 312, a slot 314, an arch wire 316, an integral hinge 320, a spring element 322, integral spring hinges 320a and 320b, a bearing protrusion 334, and an alignment marking 336.

An angled keyway 332 is provided near one end of the base 310. The cover 312 contains a corresponding locking tongue 330 that enables the ligation cover 312 to be selectively locked or unlocked relative to the bracket base 310. The ligation cover 312 is locked to bracket base 310 by closing the cover 312 so that the locking tongue 330 is inserted into angled keyway 332. In the event that the arch wire 316 pushes against the cover 312 with sufficient force to cause the cover to bulge upwardly relative to the bracket base 310, rather than causing the tongue 330 to withdraw from the angled keyway 332, which could result in undesired disengagement of the cover 312, the locking tongue 330 is instead pulled more deeply into the angled keyway 332, thereby tightening the locking mechanism. This provides added safety, and in order to open the cover, the locking tongue 330 is pulled out of angled keyway 332 and over the nose of bracket base 310.

This example includes a temporarily visible mark 336 (which may be either formed with removable or indelible ink) formed on the underside of the ligation cover 312. The temporarily visible mark 336 is either removable or not visible when hidden under the ligation during long term use of the bracket 300 to straighten teeth. The temporarily visible mark 336 illustrated in FIG. 3A includes a numeral "3" in the upper left quadrant of an alignment grid, indicating that this bracket is intended for use on a tooth of the upper left quadrant of the patient's teeth. The number "3" indicates that the bracket is intended for a tooth corresponding to the number "3" (e.g., the canine or cuspid in the upper left hand quadrant of the patient's teeth)

Figure 4A:
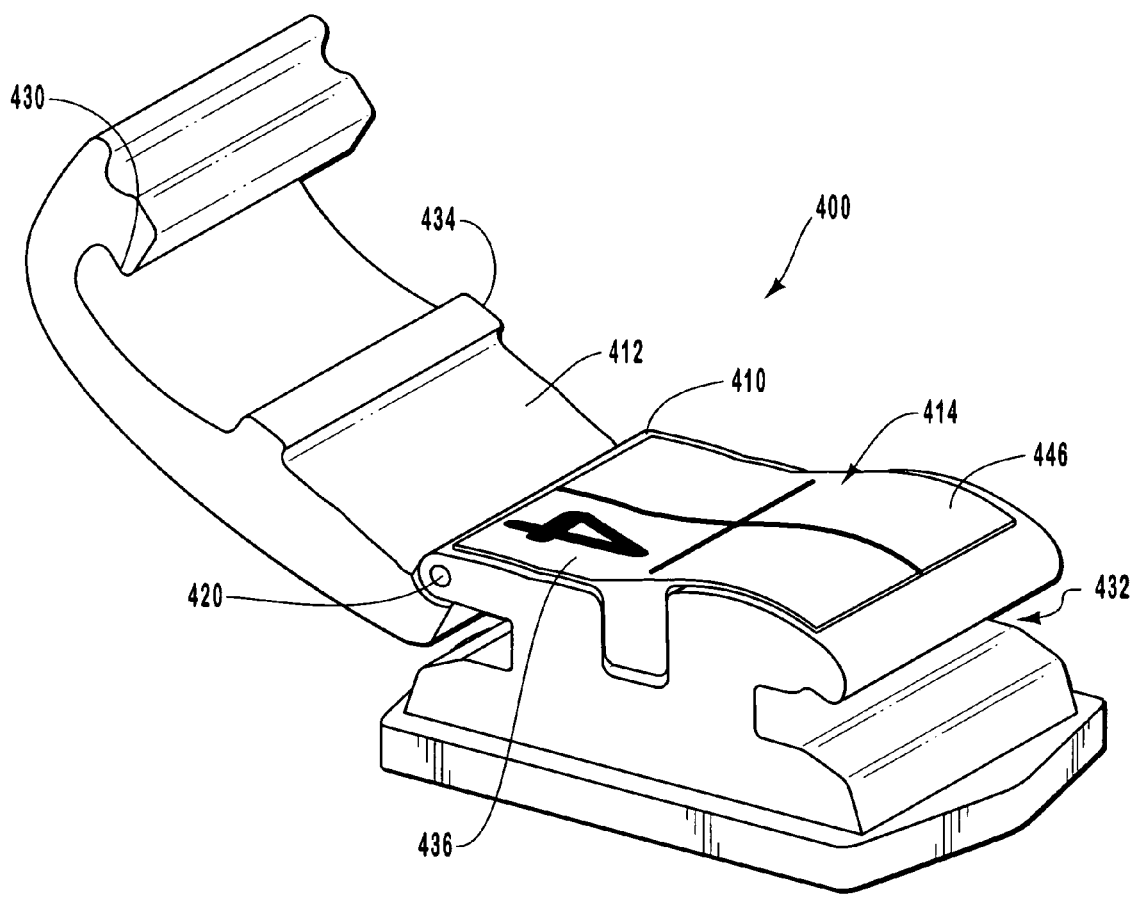
FIGS. 4A–4B are perspective views that illustrate an exemplary self-ligating orthodontic bracket that includes a removable auxiliary cover that fits over the bracket base and that includes or defines a temporarily visible mark.
Figure 4B:
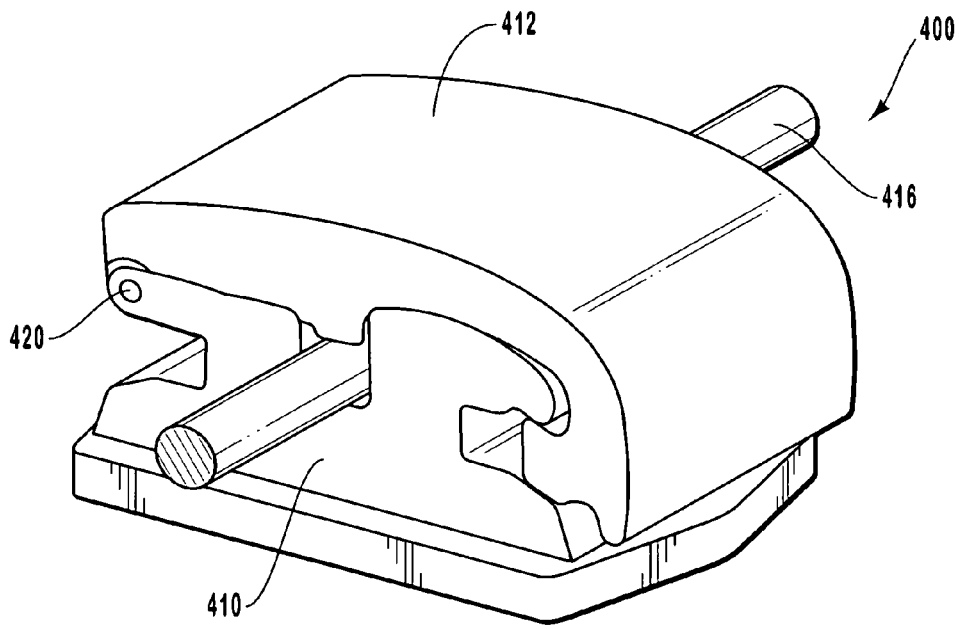

Another example of an alternative bracket 400 implementing the invention is shown in FIGS. 4A–4B. This bracket includes a base 410, a ligation cover 412, a slot 414, an arch wire 416, a locking ridge 430, a locking recess 432, a bearing protrusion 434, an alignment marking 436, and a removable auxiliary cover 446. This example includes a pin hinge 420 rather than one of the various types of hinges of the previous examples. A hinge of this type may be desirable where the cover and base are made of metal, two dissimilar materials or where it is desired to separately manufacture the bracket base and ligation cover and then hingedly attach thereon.

The temporarily visible mark 436 is positioned on a removable auxiliary cover 446. According to one embodiment, the removable auxiliary cover 446 may fit over the bracket base 410 by engaging the arch wire slot 414 of bracket 400 when the ligation cover 412 is in an open position. The temporarily visible mark 436 on auxiliary cover 446 may be formed with water soluble or indelible ink. Once the bracket 400 has been properly placed onto a tooth, the removable auxiliary cover 446 is removed and discarded. FIG. 4B illustrates the bracket 400 with the temporary cover plate 446 removed and the cover 412 closed.

The alignment marking 436 illustrated in FIG. 4A includes a numeral "4" in the lower right quadrant of an alignment grid, indicating that this bracket is intended for use on a tooth of the lower right quadrant of the patient's teeth. The number "4" indicates that the bracket is intended for a tooth corresponding to the number "4" (e.g., the first bicuspid within the lower right quadrant of the patient's teeth).

Figure 5A:
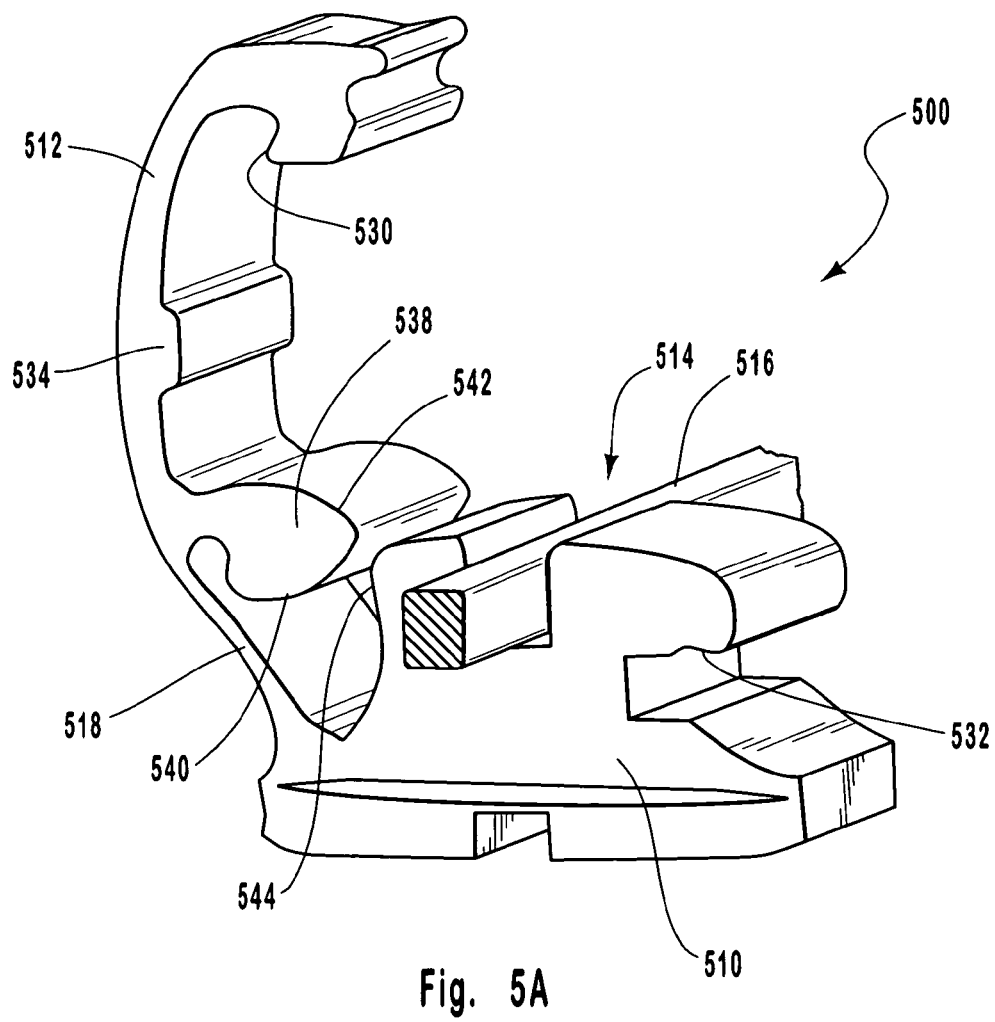
FIGS. 5A–5B are perspective views that illustrate an exemplary self-ligating orthodontic bracket that includes a temporarily visible mark on a labial surface of the ligation cover.
Figure 5B:
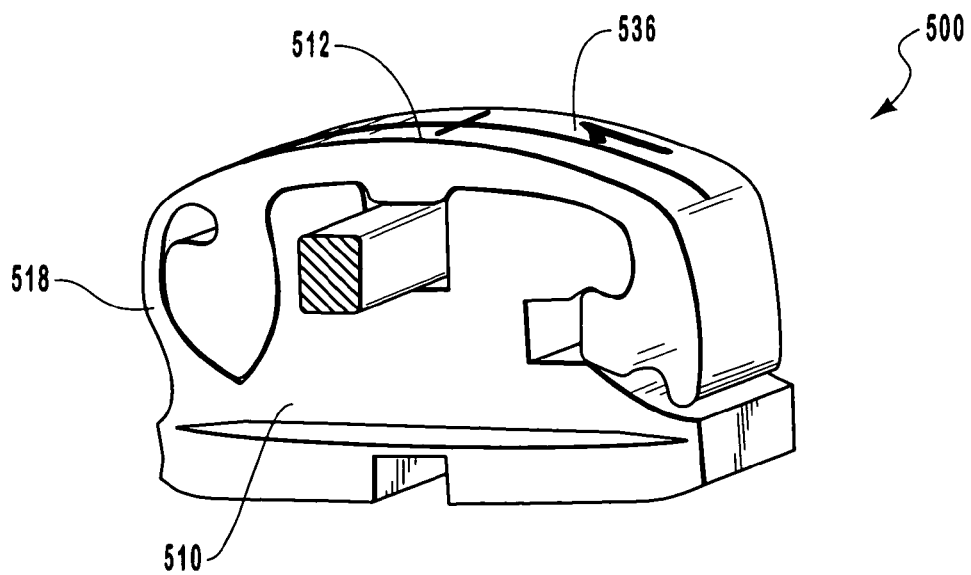

Yet another example of an alternative bracket 500 implementing the invention is shown in FIGS. 5A–5B. The orthodontic bracket 500 includes a base 510, a cover 512, an arch wire slot 514, an arch wire 516, a locking tongue 530, an angled keyway 532, and a bearing protrusion 534. The cover 512 is hingedly connected to the bracket base 510 by a single elongated film hinge 518. The elongated film hinge 518 preferably has a length and thickness that are selected so that the hinge 518 has a desired level of strength, flexibility and resilience. The film hinge 518 of this embodiment is designed to bend along substantially its entire length rather than at a single point or line. This helps the hinge resist fatigue or fracture better than film hinges that bend along a single line.

The bracket 500 further includes an interactive cam structure 538 with a first curved surface 540 and a second curved surface 542. The first curved surface 540 interacts with the elongated film hinge 518 to provide a curved surface that helps ensure that the elongated film hinge 518 bends gradually over its entire length rather than abruptly at any specific locale. The second curved surface 542 is curved in such a way so that it interacts with a corresponding wall 544 of the base 510 so to bias the ligation cover 512 in an open position relative to the bracket base 510 when the ligation cover 512 is in the open position. This improves access to arch wire slot 514, making insertion or removal of the arch wire 516 easier. The second curved surface 542 may, depending on the shape of the corresponding wall 544 of the bracket base 510, also act to bias the ligation cover 512 to remain in a closed position when in the closed position relative to the bracket base 510.

The temporarily visible mark 536 illustrated in FIG. 5B includes a numeral "1" in the lower right quadrant of an alignment grid, indicating that this bracket is intended for use on a tooth of the lower right quadrant of the patient's teeth. The number "1" indicates that the bracket is intended for a tooth corresponding to the number "1" (e.g., the first incisor within the lower right quadrant of the patient's teeth).

Figure 6A:
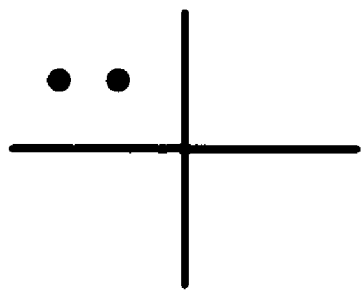
FIGS. 6A–6D illustrate marks that may be used instead of characters on an orthodontic bracket to designate which tooth or subset of teeth a particular bracket pertains.
Figure 6B:
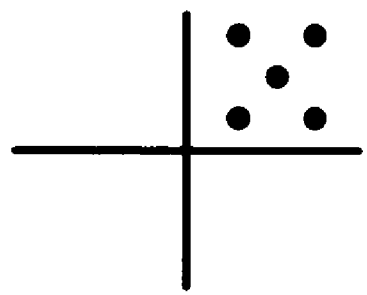
Figure 6C:
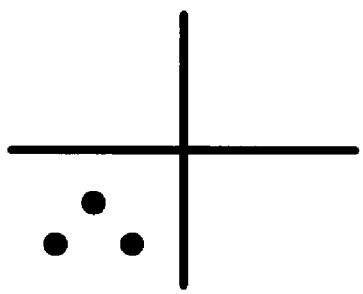
Figure 6D:
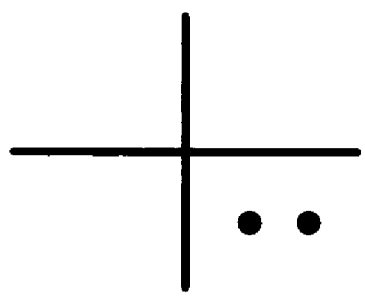

FIGS. 6A–6D illustrate an alternative bracket selection system that includes an alignment grid and one or more dots rather than characters to designate which tooth a bracket pertains. The marking depicted in FIG. 6A includes two dots, which may be used to indicate that the bracket should be attached to the second tooth from the center on the upper left quadrant of the patient's teeth. FIG. 6B shows five dotes, which may correspond to a bracket that is to be placed onto the fifth tooth from the center in the upper right quadrant of the person's teeth. FIG. 6C shows three dots, which may correspond to a bracket that is to be placed onto the third tooth from the center in the lower left quadrant of the person's teeth. FIG. 6D shows two dots, which may correspond to a bracket that is to be placed onto the second tooth from the center in the lower right quadrant of the person's teeth.

Figure 7A:
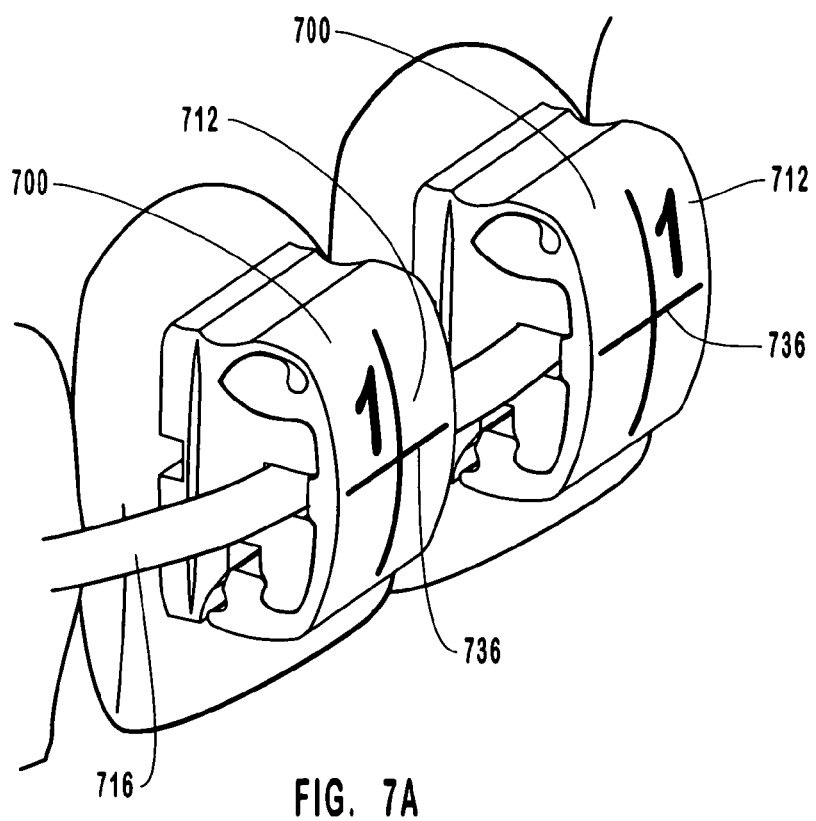
FIG. 7A is perspective view that illustrates two orthodontic brackets that include temporarily visible marks and that are attached to adjacent upper incisors.
Figure 7B:
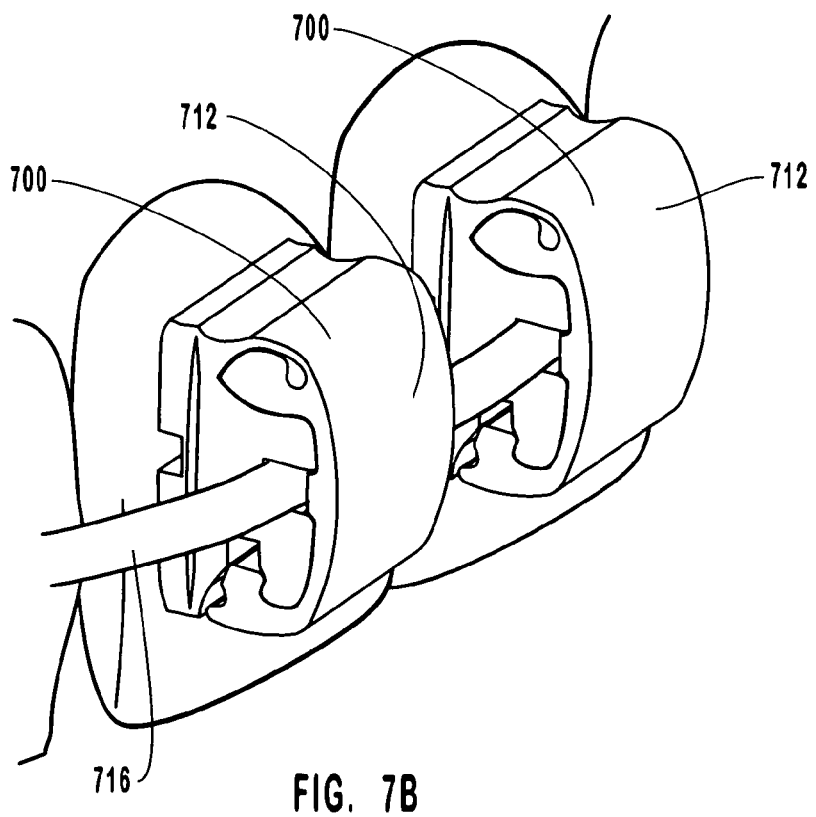
FIG. 7B illustrates the orthodontic brackets of FIG. 7A, but with the temporarily visible marks having been removed.

FIG. 7A illustrates a pair of brackets 700 that have been placed on the upper incisors of a patient and which include temporarily visible marks, more particularly, removable markings 736. An exemplary arch wire 716 is also shown together with the brackets 700. The bracket on the upper left first incisor includes the number "1" in the upper left quadrant of an alignment grid on the ligation cover 712, while the bracket on the upper right first incisor includes a "1" in the upper right quadrant of an alignment grid on the cover 712. The number "1" and the placement of the number within a particular quadrant identify which tooth the bracket corresponds to. The alignment grid on the front surface of the cover 712 may also be used during placement of the bracket in order to properly align the bracket horizontally and/or vertically on the tooth of the patient. FIG. 7B illustrates the brackets 700 after the removable markings 736 have been removed (e.g., by rinsing or washing away water soluble ink or by removing a decal with the markings 736).

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An orthodontic bracket comprising:
   a bracket base;
   at least one arch wire slot in said bracket base adapted to receive an arch wire therein;
   a ligation cover for ligating an arch wire in said arch wire slot that can be selectively moved relative to said bracket base between an open non-ligating position relative to said arch wire slot and a closed, ligating position relative to said arch wire slot; and
   temporary marking means for temporarily providing a mark on a bracket that is visible during placement of the bracket onto a tooth but that does not remain visible during use of the bracket to straighten teeth, wherein said temporary marking means comprises an alignment grid defining four quadrants and a marking within one of said quadrants, and wherein said marking within one of said quadrants comprises a character that is a letter or a number or a representation of a letter or number.

2. An orthodontic bracket as recited in claim 1, wherein said temporary marking means comprises a removable marking on a labial surface of said ligation cover.

3. An orthodontic bracket as recited in claim 1, wherein said temporary marking means comprises a removable or permanent marking on a surface of said bracket base that is exposed when said ligation cover is in the open, non-ligating position.

4. An orthodontic bracket as recited in claim 1, wherein said temporary marking means comprises a removable or permanent marking on an underside of said ligation cover.

5. An orthodontic bracket as recited in claim 1, wherein said temporary marking means comprises or forms part of a removable auxiliary cover that is removably attached to a surface of said bracket base.

6. An orthodontic bracket as recited in claim 1, wherein said ligation cover is hingedly attached to said bracket base.

7. An orthodontic bracket as recited in claim 1, wherein said bracket base and said ligation cover are integrally formed together as a single piece of plastic.

8. An orthodontic bracket as recited in claim 1, wherein at least one of said bracket base or said ligation cover comprises metal.

9. An orthodontic bracket as recited in claim 1, wherein said marking within one of said quadrants is a representation of a number that comprises one or more dots.

10. An orthodontic bracket as recited in claim 1, wherein said temporary marking means comprises a water soluble ink.

11. An orthodontic bracket as recited in claim 1, wherein said temporary marking means is printed on a decal that is removably attached to the bracket.

12. An orthodontic bracket comprising:
   a bracket base;
   at least one arch wire slot within said bracket base adapted to receive an arch wire therein;
   a ligation cover for ligating an arch wire in said arch wire slot that can be selectively moved relative to said bracket base between an open non-ligating position relative to said arch wire slot and a closed, ligating position relative to said arch wire slot; and
   a temporarily visible mark on a surface of said ligation cover and that is visible during placement of the orthodontic bracket onto a tooth but that does not remain visible during use of the orthodontic bracket in straightening teeth, wherein said temporarily visible mark comprises an alignment grid defining four quadrants and a marking within one of said quadrants, and wherein said marking within one of said quadrants comprises a character that is a letter or a number or a representation of a letter or number.

13. An orthodontic bracket as recited in claim 12, wherein said temporarily visible mark comprises a removable marking on a labial surface of said ligation cover.

14. An orthodontic bracket as recited in claim 12, wherein said temporarily visible mark comprises a removable or permanent marking on an underside of said ligation cover.

15. An orthodontic bracket comprising:
   a bracket base;
   at least one arch wire slot within said bracket base adapted to receive an arch wire therein;
   a ligation cover for ligating an arch wire in said arch wire slot that can be selectively moved relative to said bracket base between an open non-ligating position relative to said arch wire slot and a closed, ligating position relative to said arch wire slot; and
   a temporarily visible mark on a surface of said bracket base and that is visible during placement of the orthodontic bracket onto a tooth but that does not remain visible during use of the orthodontic bracket in straightening teeth, wherein said temporarily visible mark comprises an alignment grid defining four quadrants and a marking within one of said quadrants, and wherein said marking within one of said quadrants comprises a character that is a letter or a number or a representation of a letter or number.

16. An orthodontic bracket as recited in claim 15, wherein said temporarily visible mark comprises a removable or permanent marking on a surface of said bracket base that is exposed when said ligation cover is in the open, non-ligating position.

17. An orthodontic bracket as recited in claim 15, wherein said temporarily visible mark comprises or forms part of a removable auxiliary cover that is removably attached to a surface of said bracket base.

18. An orthodontic bracket kit comprising a plurality of orthodontic brackets as recited in claims 1, 12 or 15, wherein at least two of said orthodontic brackets are designed for placement on different teeth of a patient.

19. An orthodontic bracket kit as recited in claim 18, wherein each orthodontic bracket pertains to a specific tooth of a patient.

20. A method for placing an orthodontic bracket onto a person's teeth, comprising:
   (a) providing an orthodontic bracket as recited in claims 1, 12 or 15;
   (b) associating the orthodontic bracket with a particular tooth or subset of teeth of the patient; and
   (c) attaching the orthodontic bracket to the particular tooth or to a tooth of the subset of teeth.

21. A method as recited in claim 20, wherein (b) is carried out according to a tooth-selection marking on the orthodontic bracket.

22. A method as recited in claim 20, further comprising aligning the orthodontic bracket on the tooth using a bracket alignment marking associated with the orthodontic bracket.

23. A method as recited in claim 20, further comprising repeating acts (a)–(c) for one or more additional orthodontic brackets.

* * * * *

UNITED STATES PATENT AND TRADEMARK OFFICE
CERTIFICATE OF CORRECTION

| | | |
|---|---|---|
| PATENT NO. | : 7,094,052 B2 | Page 1 of 1 |
| APPLICATION NO. | : 10/837460 | |
| DATED | : August 22, 2006 | |
| INVENTOR(S) | : Abels et al. | |

It is certified that error appears in the above-identified patent and that said Letters Patent is hereby corrected as shown below:

Column 2
Line 40, after "substantially", insert --horizontal line that helps in vertically aligning the bracket on the tooth. In yet another--

Column 9
Line 36, after "shows five" change "dotes" to --dots--

Signed and Sealed this

Third Day of July, 2007

JON W. DUDAS
*Director of the United States Patent and Trademark Office*